US00PP19293P2

(12) United States Plant Patent
Kobayashi

(10) Patent No.: US PP19,293 P2
(45) Date of Patent: Oct. 7, 2008

(54) POINSETTIA PLANT NAMED 'PER1180'

(50) Latin Name: *Euphorbia pulcherrima*
Varietal Denomination: PER1180

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 11/804,338

(22) Filed: May 17, 2007

(51) Int. Cl.
*A01H 5/00* (2006.01)

(52) U.S. Cl. ..... Plt./307; Plt./303

(58) Field of Classification Search ..... Plt./307, Plt./303
See application file for complete search history.

*Primary Examiner*—Annette H Para
*Assistant Examiner*—S. B. McCormick-Ewoldt
(74) *Attorney, Agent, or Firm*—C. A. Whealy

(57) ABSTRACT

A new and distinct cultivar of Poinsettia plant named 'PER1180', characterized by its uniform, upright, outwardly spreading and mounded plant habit; vigorous growth habit; freely branching habit; dark green-colored leaves; mid-season flowering response; inflorescences with dark orange-colored flower bracts; and excellent post-production longevity.

1 Drawing Sheet

Botanical designation: *Euphorbia pulcherrima.*
Cultivar denomination: 'PER1180'.

BACKGROUND OF THE INVENTION

The present invention relates to a new and distinct cultivar of Poinsettia plant, botanically known as *Euphorbia pulcherrima* Willd., and hereinafter referred to by the name 'PER1180'.

The new Poinsettia a product of a planned breeding program conducted by the Inventor in Encinitas, Calif. The objective of the breeding program is to create new Poinsettia cultivars having flower bracts with desirable colors, uniform plant habit and excellent post-production longevity.

The new Poinsettia originated from a cross-pollination made by the Inventor in December, 2002 of a proprietary selection of *Euphorbia pulcherrima* Willd. identified as code number 02-3535, not patented, as the female, or seed, parent, with a proprietary Poinsettia selection identified as PE1-1, not patented, as the male, or pollen, parent. The cultivar PER1180 was discovered and selected by the Inventor as a flowering plant within the progeny of the stated cross-pollination in a controlled greenhouse environment in Encinitas, Calif. in December, 2003. The selection of this plant was based on its attractive flower bract colors and good plant form and substance.

Asexual reproduction of the new Poinsettia by terminal vegetative cuttings in a controlled environment in Encinitas, Calif., since January, 2004, has shown that the unique features of this new Poinsettia are stable and reproduced true to type in successive generations of asexual reproduction.

SUMMARY OF THE INVENTION

The cultivar PER1180 has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'PER1180'. These characteristics in combination distinguish 'PER1180' as a new and distinct cultivar of Poinsettia:

1. Uniform, upright, outwardly spreading and mounded plant habit.
2. Vigorous growth habit.
3. Freely branching habit.
4. Dark green-colored leaves.
5. Mid-season flowering response; under natural season conditions, plants flower in about nine weeks in Encinitas, Calif.
6. Inflorescences with dark orange-colored flower bracts.
7. Excellent post-production longevity.

In side-by-side comparisons conducted in Encinitas, Calif. plants of the new Poinsettia differed primarily from plants of the female parent selection in plant uniformity and leaf color.

In side-by-side comparisons conducted in Encinitas, Calif., plants of the new Poinsettia differed primarily from plants of the male parent selection in flower bract shape.

Plants of the new Poinsettia can be compared to plants of the Poinsettia cultivar Eckadire, disclosed in U.S. Plant Pat. No. 12,846. In side-by-side comparisons conducted in Encinitas, Calif., plants of the new Poinsettia differed from plants of the cultivar Eckadire in the following characteristics:

1. Plants of the new Poinsettia were less vigorous than plants of the cultivar Eckadire.
2. Plants of the new Poinsettia and cultivar Eckadire differed in flower bract color.

Plants of the new Poinsettia can also be compared to plants of the Poinsettia cultivar Peterstar, disclosed in U.S. Plant Pat. No. 8,259. In side-by-side comparisons conducted in Encinitas, Calif., plants of the new Poinsettia differed from plants of the cultivar Peterstar in the following characteristics:

1. Plants of the new Poinsettia had darker green-colored leaves than plants of the cultivar Peterstar.
2. Plants of the new Poinsettia and the cultivar Peterstar differed in flower bract shape.

3. Plants of the new Poinsettia and cultivar Peterstar differed in flower bract color.

BRIEF DESCRIPTION OF THE PHOTOGRAPHS

The accompanying photographs illustrate the overall appearance of the new Poinsettia. These photographs show the colors as true as it is reasonably possible to obtain in colored reproductions of this type. Colors in the photographs may differ slightly from the color values cited in the detailed botanical description which accurately describe the colors of the new Poinsettia.

The photograph at the bottom of sheet comprises a side perspective view of a typical flowering plant of 'PER1180' grown in a container.

The photograph at the top of the sheet is a close-up view of a typical inflorescence of 'PER1180'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and the following observations and measurements describe plants grown in Encinitas, Calif. during the spring in a polyethylene-covered greenhouse and under conditions and practices which approximate those generally used in commercial Poinsettia production. During the production of the plants, day temperatures averaged 24° C., night averaged 19° C. and light levels were about 4,000 foot-candles. Measurements and numerical values represent averages for typical flowering plants. Single plants were grown in 16.5-cm pots and pinched one time. Plants were about 14 weeks old when the photographs and the detailed description were taken.

Botanical classification: *Euphorbia pulcherrima* cultivar PER1180.

Parentage:

*Female, or seed, parent.*—Proprietary selection of *Euphorbia pulcherrima* Willd. identified as code number 02-3535, not patented.

*Male, or pollen, parent.*—Proprietary selection of *Euphorbia pulcherrima* Willd. identified as code number PE1-1, not patented.

Propagation:

*Type.*—Terminal vegetative cuttings.

*Time to initiate roots.*—About ten days at 20° C. to 22° C.

*Time to produce a rooted young plant.*—About four weeks at 20° C. to 22° C.

*Root description.*—Fibrous; white in color.

Plant description:

*Plant habit and form.*—Uniform, upright, outwardly spreading and mounded plant habit; inverted triangle. Inflorescences positioned above the foliar plant. Vigorous growth habit.

*Plant height.*—About 26 cm.

*Plant diameter or spread.*—About 38 cm.

*Lateral branch description.*—Quantity: Freely branching habit, about ten lateral branches develop after pinching. Length: About 19 cm. Diameter: About 6 mm. Internode length: About 1.8 cm. Strength: Strong. Texture: Smooth, glabrous. Color: 146A.

*Foliage description.*—Arrangement: Alternate, simple. Length: About 11.2 cm. Width: About 7.2 cm. Shape: Elliptical; lobed. Apex: Acuminate. Base: Attenuate. Margin: Entire with lobes. Venation pattern: Pinnate. Texture, upper surface: Smooth, glabrous. Texture, lower surface: Slightly pubescent. Surface: Rugose. Color: Developing foliage, upper surface: 147A. Developing foliage, lower surface: 147B. Fully expanded foliage, upper surface: 147A; venation, 146B. Fully expanded foliage, lower surface: Darker than 147A; venation, 146C. Petiole: Length: About 4.6 cm. Diameter: About 2.5 mm. Texture, upper and lower surfaces: Smooth, glabrous. Color, upper and lower surfaces: 182B.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent. Inflorescences positioned above the foliage.

*Natural flowering season.*—Autumn/winter; inflorescence initiation and development is induced under long nyctoperiod conditions. Mid-season flowering; response time, about nine weeks under natural season conditions in Encinitas, Calif.

*Post-production longevity.*—Excellent post-production longevity; plants of the new Poinsettia maintain good substance and bract color for about four weeks under interior conditions.

*Inflorescence size.*—Diameter: About 30 cm. Height (depth): About 4.5 cm.

*Flower bracts.*—Quantity per inflorescence: About 28. Length, largest bracts: About 13 cm. Width, largest bracts: About 10.3 cm. Shape: Elliptical, lobed. Apex: Acuminate. Base: Attenuate. Margin: Entire with shallow lobes. Texture, upper and lower surfaces: Smooth, glabrous. Aspect; Horizontal; slightly recurved. Venation pattern: Pinnate. Color: Developing or transitional bracts, upper surface: 45A. Developing or transitional bracts, lower surface: 47B. Fully developed bracts, upper surface: 43B. Fully developed bracts, lower surface: 39B. Venation, upper and lower surfaces: Similar to flower bract color. Bract petiole: Length: About 3.8 cm. Diameter: About 2 mm. Texture, upper and lower surfaces: Smooth, glabrous. Color, upper and lower surfaces: 43C.

*Cyathia.*—Quantity per corymb: About 16. Diameter of cyathia cluster: About 3 cm. Length: About 9 mm. Width: About 5 mm. Shape: Ovoid. Color, immature: 146D. Color, mature: 146C. Nectaries: Quantity per cyathium: About one or two. Size: About 3 mm by 4 mm. Color: 7A.

*Peduncles.*—Length: About 4 mm. Diameter: About 2 mm. Strength: Strong. Aspect; Upright. Texture: Smooth, glabrous. Color: 146C.

*Reproductive organs.*—Stamens: Quantity per cyathium: About 15. Anther shape: Oval; bi-lobed. Anther length: Less than 1 mm. Anther color: 53A. Amount of pollen: Scarce. Pollen color: 9A. Pistils: None observed. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 15° C. to about 30° C.

It is claimed:

1. A new and distinct Poinsettia plant named 'PER1180' as illustrated and described.

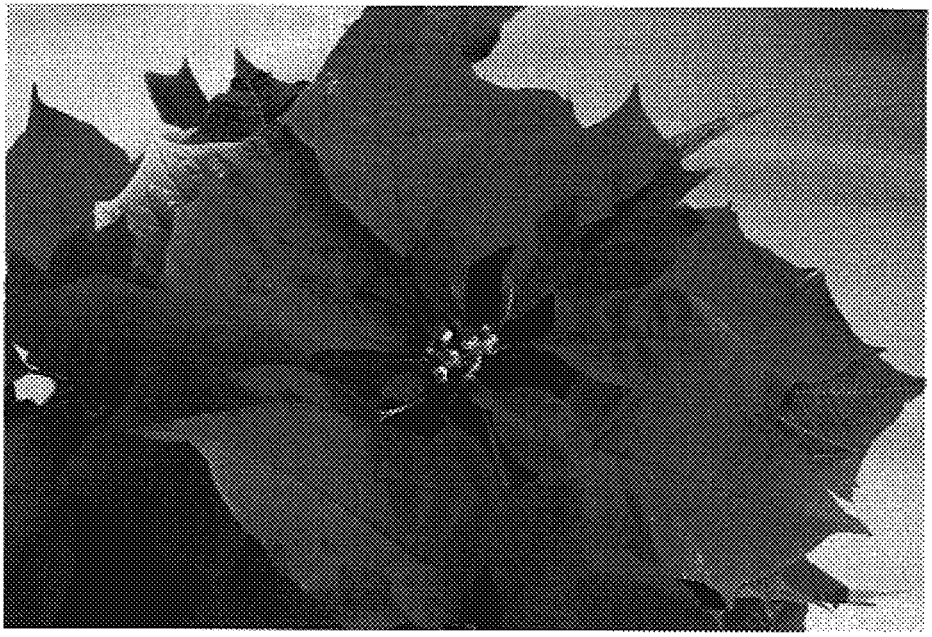
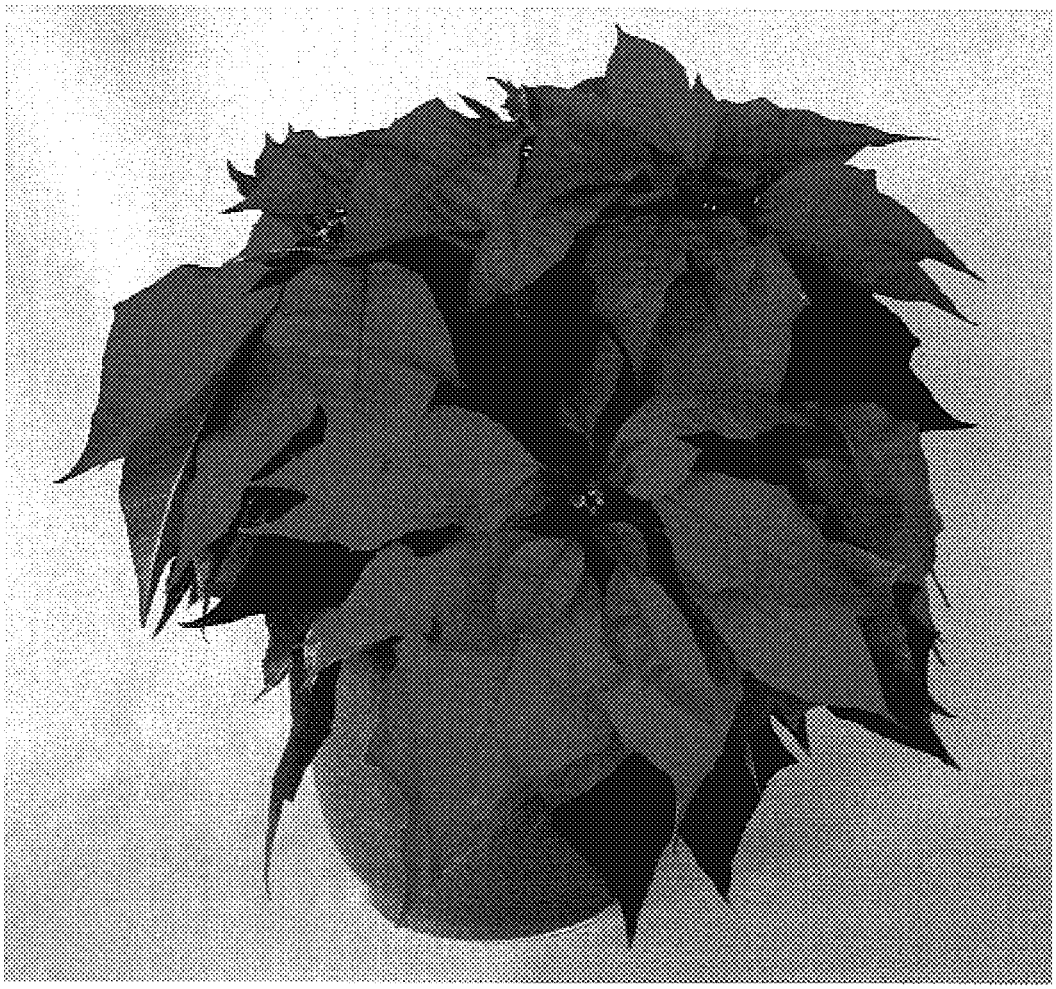

* * * * *